(12) United States Patent
Arms et al.

(10) Patent No.: US 8,136,408 B2
(45) Date of Patent: Mar. 20, 2012

(54) STRAIN SENSOR MOUNTED WITH LIGHT CURABLE ADHESIVE

(75) Inventors: Steven W. Arms, Williston, VT (US); Christoper P. Townsend, Shelburne, VT (US); Steven W. Mundell, Richmond, VT (US); David L. Churchill, Burlington, VT (US)

(73) Assignee: Microstrain, Inc., Williston, VT (US)

( * ) Notice: Subject to any disclaimer, the term of this patent is extended or adjusted under 35 U.S.C. 154(b) by 0 days.

(21) Appl. No.: 13/015,562

(22) Filed: Jan. 27, 2011

(65) Prior Publication Data

US 2011/0113892 A1    May 19, 2011

Related U.S. Application Data

(62) Division of application No. 12/211,975, filed on Sep. 17, 2008, which is a division of application No. 11/091,244, filed on Mar. 28, 2005, now Pat. No. 7,461,560.

(60) Provisional application No. 60/556,974, filed on Mar. 26, 2004.

(51) Int. Cl.
    *G01M 5/00*    (2006.01)

(52) U.S. Cl. ................ 73/786; 73/765; 73/776

(58) Field of Classification Search .......... 73/786, 73/765, 776
See application file for complete search history.

(56) References Cited

U.S. PATENT DOCUMENTS

| 3,445,800 A * | 5/1969 | Ambulos et al. ............ 338/2 |
| 6,928,881 B2 * | 8/2005 | Brennan ............ 73/766 |

OTHER PUBLICATIONS

M. Vaziri and C.-L. Chen, "Optical-fiber strain sensors with asymmetric etched structures," Applied Optics vol. 32, No. 31 (Nov. 1993).*
Arms, S.W., Townsend, C.P, "Microminiature, Temperature Compensated, Magnetoelastic Strain Gauge," SPIE's 9th Int'l Symposium on Smart Structures & Materials and 7th Int'l Symposium on Nondestructive Evaluation and Health Monitoring of Aging Infrastructure, San Diego, CA, Mar. 17-21, 2002. Accessed online at <www.microstrain.com>.*
James W. Dally and William F. Riley, "Experimental Stress Analysis." McGraw-Hill, NY, Third Edition, 1991, pp. 196-197.*

* cited by examiner

*Primary Examiner* — Lisa Caputo
*Assistant Examiner* — Punam Roy
(74) *Attorney, Agent, or Firm* — James Marc Leas (57) ABSTRACT

A device includes a structure, a strain sensor and a light curable adhesive. The structure has a structure surface. The light curable adhesive bonds the strain sensor to the structure surface.

29 Claims, 12 Drawing Sheets

STRAIN SENSOR MOUNTED WITH LIGHT CURABLE ADHESIVE

This patent application is a divisional of U.S. patent application Ser. No. 12/211,975, filed Sep. 17, 2008 which is a divisional of U.S. patent application Ser. No. 11/091,244, filed Mar. 28, 2005, now U.S. Pat. No. 7,461,560, which claimed priority of U.S. provisional patent application 60/556,974, filed Mar. 26, 2004.

RELATED US PATENT APPLICATIONS AND PAPERS

This patent application is related to the following US patents and patent applications:

U.S. Pat. No. 7,478,108 to Townsend, ("the '108 patent") "Data Collection and Storage Device," filed Dec. 6, 2000, incorporated herein by reference;

U.S. Pat. No. 7,081,693 to Hamel, et al., ("the '693 patent") "Energy Harvesting for Wireless Sensor Operation and Data Transmission," filed Mar. 5, 2003, incorporated herein by reference;

2003-0234730 to Arms, et al., ("the '730 application") "Robotic System for Powering and Interrogating Sensors," filed Mar. 5, 2003, incorporated herein by reference; and U.S. Pat. No. 7,256,505 to Arms, et al., ("the '505 patent") "Shaft Mounted Energy Harvesting for Wireless Sensor Operation and Data Transmission," filed Jan. 31, 2004 incorporated herein by reference.

This patent application is also related to a paper by Arms, S. W. et al., "Power Management for Energy Harvesting Wireless Sensors" ("the power management paper"), Proceedings SPIE Smart Structures and Smart Materials, Paper no. 5763-36, San Diego, Calif., March 2005, incorporated herein by reference.

FIELD

This patent application generally relates to a strain gauge. More particularly it relates to a way of bonding a strain gauge to a structure. Even more particularly it relates to a way to protect the strain gauge.

BACKGROUND

The quality of data reported by a strain gauge mounted to a metallic substrate depends on the integrity of the adhesive bond between the strain sensor and the substrate. It is generally accepted that the adhesive bond (typically an epoxy) breaks down in the presence of moisture. Swelling of the epoxy due to moisture absorption results in shear stresses at the epoxy/metal interface, and over time, these shear stresses can result in failure of the epoxy bond and de-lamination of the strain gauge.

One solution to this problem, often employed on large civil structures, is to package the strain gauge within a sandwich of two hermetically sealed stainless steel ribbons. Laser or electron beam is used to provide the sealing. This strain sensitive ribbon is then spot welded to the structure under test. However, this spot welding process creates localized changes in the steel's microstructure which may be subject to higher than normal rates of corrosion. For many applications of welded structures, the creation of corrosion focus points is considered unacceptable, as these could result in degradation in the physical appearance, added maintenance costs, or even the initiation of material failure. Therefore protection against moisture is desired.

None of the systems for connecting a strain sensor to a structure have been satisfactory in providing a reliable bond that is resistant to moisture degradation without affecting structural properties. In addition, when moisture degradation occurs there has been no way to recognize that data coming from the sensor is not acceptable. Thus, a better system for connecting strain sensors to structures is needed, and this solution is provided by the following.

SUMMARY

One aspect of the present patent application is a device that includes a structure, a strain sensor and a light curable adhesive. The structure has a structure surface. The light curable adhesive bonds the strain sensor to the structure surface.

DETAILED DESCRIPTION

The present inventors recognized that substantial improvement in strain sensor reliability could be achieved by providing an improved moisture barrier and by providing a self testing scheme so that delamination or other problems could be detected and the strain sensor replaced. They recognized that they could provide a for the strain sensor and fill the with wax to substantially improve resistance to moisture penetration. They also recognized that for some dielectrics capacitance of a capacitor adjacent to the strain sensor could provide data about the magnitude of moisture penetration and the potential for degradation of the epoxy bonding the strain sensor to the substrate surface to which it is mounted. They also recognized that the scheme could also be used to monitor the curing of the epoxy or of other polymers.

The structure to which the strain sensor may be attached may be a building, a bridge, or a vehicle, such as a car, a truck, a ship, construction equipment, or excavation machinery. The structure can also be the spinning shaft of a motor, pump, generator or other spinning device.

Figure 1A:
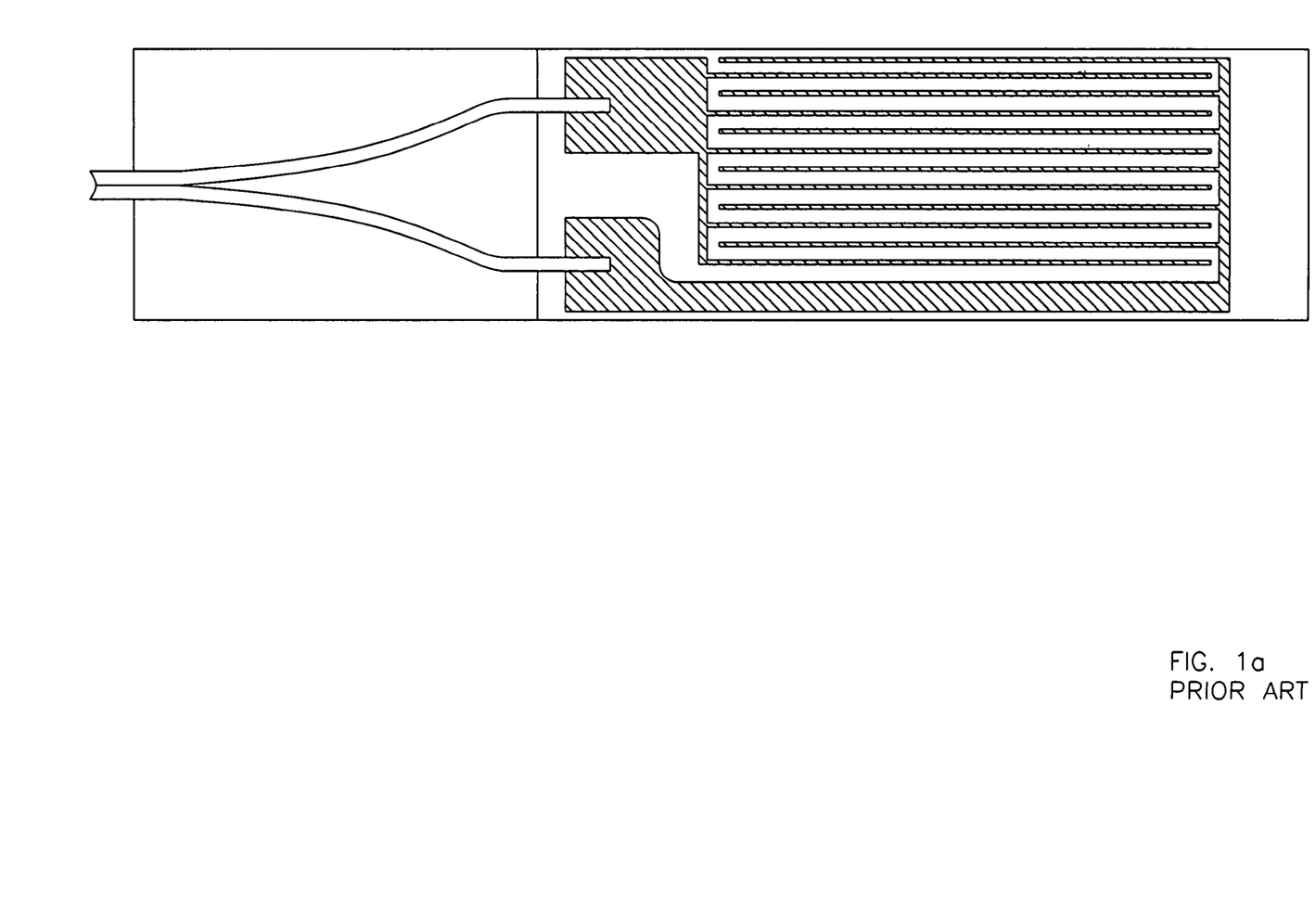
FIG. 1a is a top view of a prior art dielectrometer for cure monitoring of composite materials with a comb like structure.

A hard-wired system that uses a comb-like structure patterned on polyimide as a dielectrometer for cure monitoring of composite materials are described in a manual, "Eumetric 100A Dielectrometer Cure Monitoring System User's Guide," available from Holometrix, formerly Micromet, Newton Centre, Mass. and shown in FIG. 1a. The dielectrometer reflects the degree of cross-linking of the polymer chains, which can be related to strength. Higher dielectric constants indicate stronger material properties.

Figure 1B:
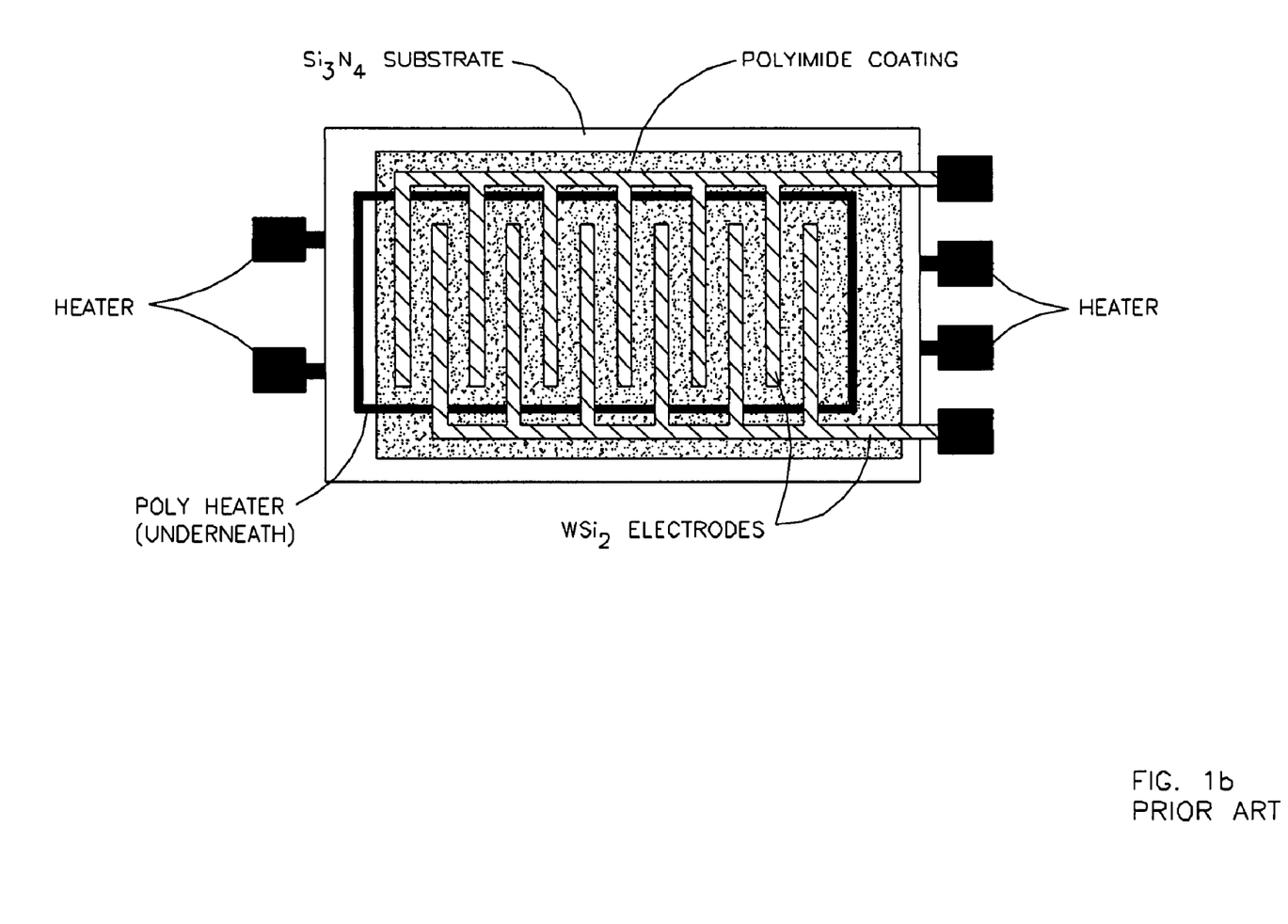
FIG. 1b is a top view of a prior art humidity sensor with a comb like sructure.

The dielectric constant measured in such a device is greatly influenced by the presence of moisture because the dielectric constant of air is one, but the dielectric constant of water is 80. A patterned humidity sensor developed at Dublin City University is described in a paper, "Humidity Sensors," and includes a comb-like structure, as shown in FIG. 1b. This sensor uses polyimide as the moisture sensing dielectric material because of its excellent thermal and electrical stability. It also uses a silicon nitride substrate.

Such a capacitance monitoring technique has not previously been used to monitor moisture in the vicinity of a strain gauge's epoxy bond or attachment to the surface of the structure to which the strain gauge is affixed.

The present strain sensing system has the ability to monitor and report on the integrity of its own encapsulation by monitoring the moisture content of the epoxy or the moisture content adjacent to the epoxy. Self-testing of the integrity of the encapsulation is accomplished by measuring the capacitance of a capacitance sensor that is sensitive to the presence of moisture in the vicinity of the strain gauge/epoxy glue line attachment to the metal or other material of the structure to which it is affixed.

Figure 2A:
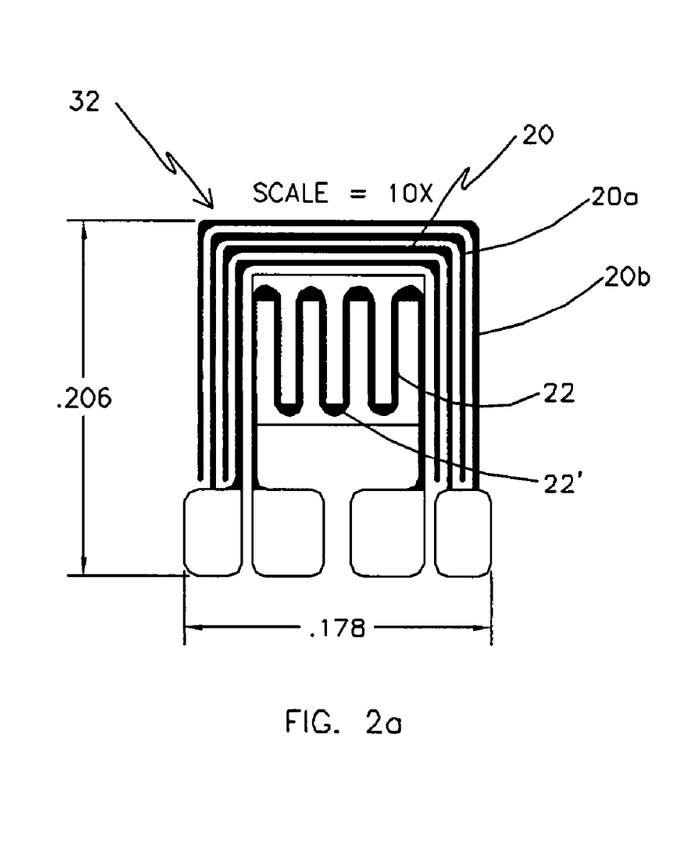
FIG. 2a is a top view of one embodiment of a patterned capacitance sensor integrated with a strain gauge.
Figure 2B:
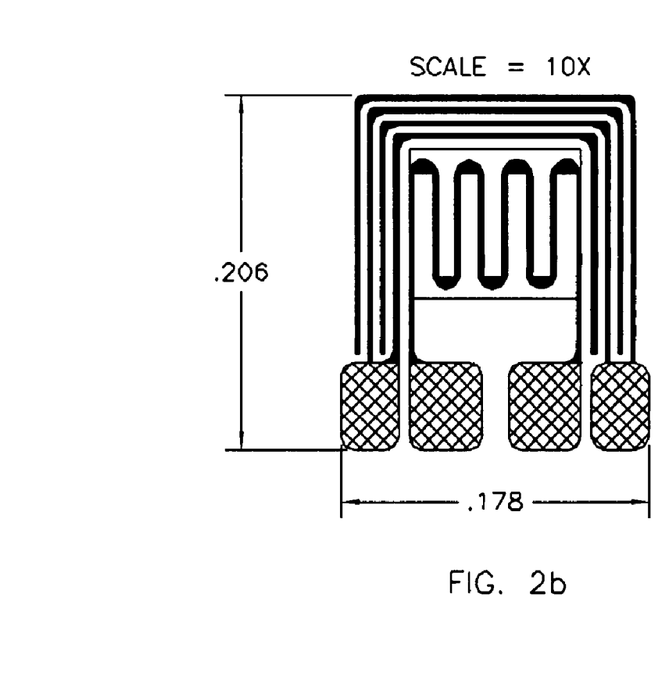
FIG. 2b is a top view of another embodiment of a patterned capacitance sensor integrated with a strain gauge in which pads are formed of windows or stripes of metal in the bonding pad area.

Patterned capacitance sensor 20 is integrated with and provided around the periphery of strain gauge 22, as shown in top view in FIGS. 2a, 2b. Patterned capacitance sensor 20 includes interdigitated comb metal plates 20a, 20b on polyimide substrate 24, such as a Kapton substrate, as shown in cross section in FIG. 3a. As shown, patterned capacitance sensor 20 is located on three sides of small 5000 ohm strain gauge 22, such as the Micro-Measurements model N3K-06-S022H-50C/DP. Capacitance sensor 20 is preferably un-encapsulated and its polyimide substrate 24 is preferably in direct contact with the same epoxy adhesive 26 used to affix strain gauge 22 to surface 28 of structure 30.

Figure 3A:
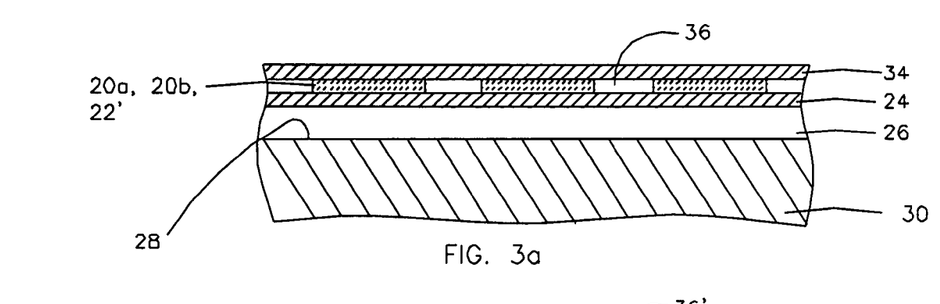
FIGS. 3a-3c are cross sectional views of different embodiments of the capacitance sensor integrated with the strain gauge of FIGS. 2a, 2b with air, polyimide, and epoxy dielectrics.

Capacitance sensor 20 and strain sensor 22 are both fabricated by lithographically providing metal lines 20a, 20b, 22' on polyimide substrate 24, as shown in FIG. 3a. Sensor assembly 32, including capacitance sensor 20 and strain sensor 22, are preferably epoxy bonded with epoxy 26 to surface 28 of structure 30, such as a machine, bridge, vehicle or any other structure. In one embodiment, shown in FIG. 3a, polyimide cap 34 is provided to protect metal lines 20a, 20b, 22' from mechanical damage. Capacitance of capacitance sensor 20 changes as moisture content of air dielectric 36 between plates 20a, 20b of capacitance sensor 20 changes.

Figure 3B:
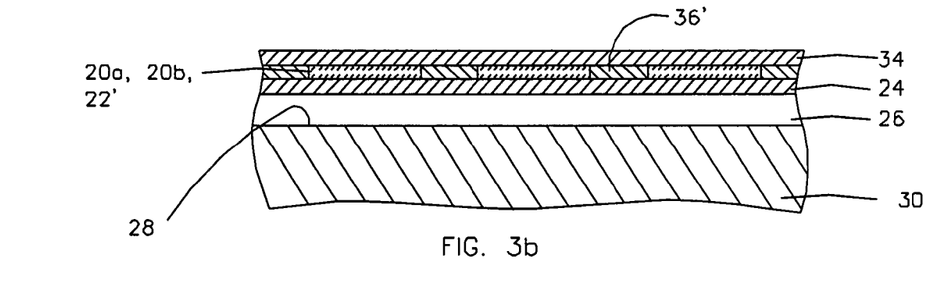
Figure 3C:
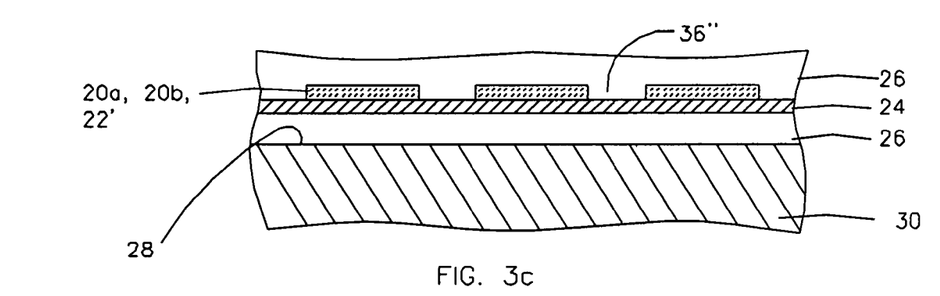

In another embodiment, polyimide dielectric 36', or another polymer that has a dielectric constant sensitive to the presence of moisture, is provided between plates 20a, 20b of capacitance sensor 20, as shown in FIG. 3b. Alternatively, polyimide cap 34 is omitted and mounting epoxy is itself provided on the surface of capacitance sensor 20 and between metal plates 20a, 20b to provide epoxy dielectric 36" between plates 20a, 20b of capacitance sensor 20, as shown in FIG. 3c. Should moisture reach mounting epoxy 26, it will also be present in air dielectric 36, polyimide dielectric 36', or epoxy dielectric 36", and change the capacitance of capacitance sensor 20.

In another approach, capacitance of the strain sensor itself is used as the moisture sensor. While electrical contact to the surface 28 of structure 30 would provide a two plate capacitance with polyimide substrate 24 and mounting epoxy 26 serving as the dielectric in that case, no electrical contact to the structure surface is actually needed. With a high frequency signal applied across strain gauge 22, as described herein above for separate capacitance sensor 20, changes in dielectric properties in its neighborhood could be detected, including changes from moisture penetration adjacent strain gauge 22.

Figure 4A:
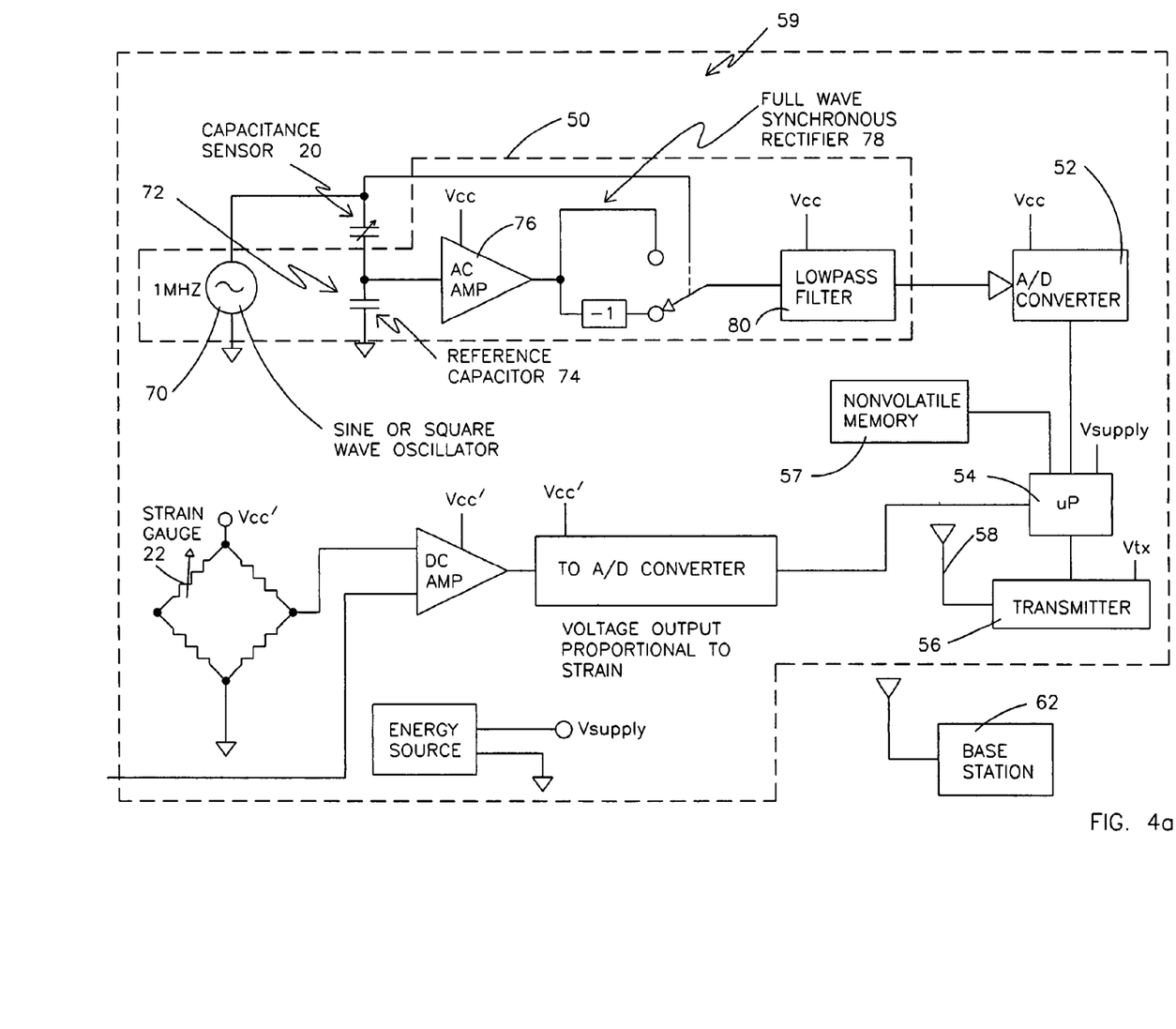
FIG. 4a is a schematic/block diagram of an embodiment including a sensor node and a base station in which the sensor node has both a strain gauge and a moisture sensor.

The change in capacitance of capacitance sensor 20 is detected by capacitance signal conditioning circuit 50, A/D converter 52, and microprocessor 54 and transmitted externally by transmitter 56 through antenna 58, as shown in FIG. 4a. These components are all located on circuit board 59 that is also bonded to surface 28 of structure 30. Base station 62 receives transmission from antenna 58 and from other sensor nodes that may be nearby. Signal conditioning circuit 50 includes, sine or square wave oscillator 70 that provides a high frequency signal to capacitive divider 72 that includes capacitance sensor 20 and reference capacitor 74. Reference capacitor 74 has an inorganic dielectric and is insensitive to changes in humidity. Output of capacitance divider 72 will track changes in capacitance in humidity sensitive capacitance sensor 20, and this signal is amplfied in AC amplifier 76, rectified in full wave synchronous rectifier 78, and filtered in low pass filter 80 to provide a DC output proportional to the difference in capacitance between capacitors 20 and 74. If this number stays constant then capacitance sensor 20 has not changed and humidity has not entered. Thus, the present invention provides self-testing of the integrity of the epoxy bond between sensor assembly 32 and structure surface 28 and wireless transmission of the integrity data.

Figure 4B:
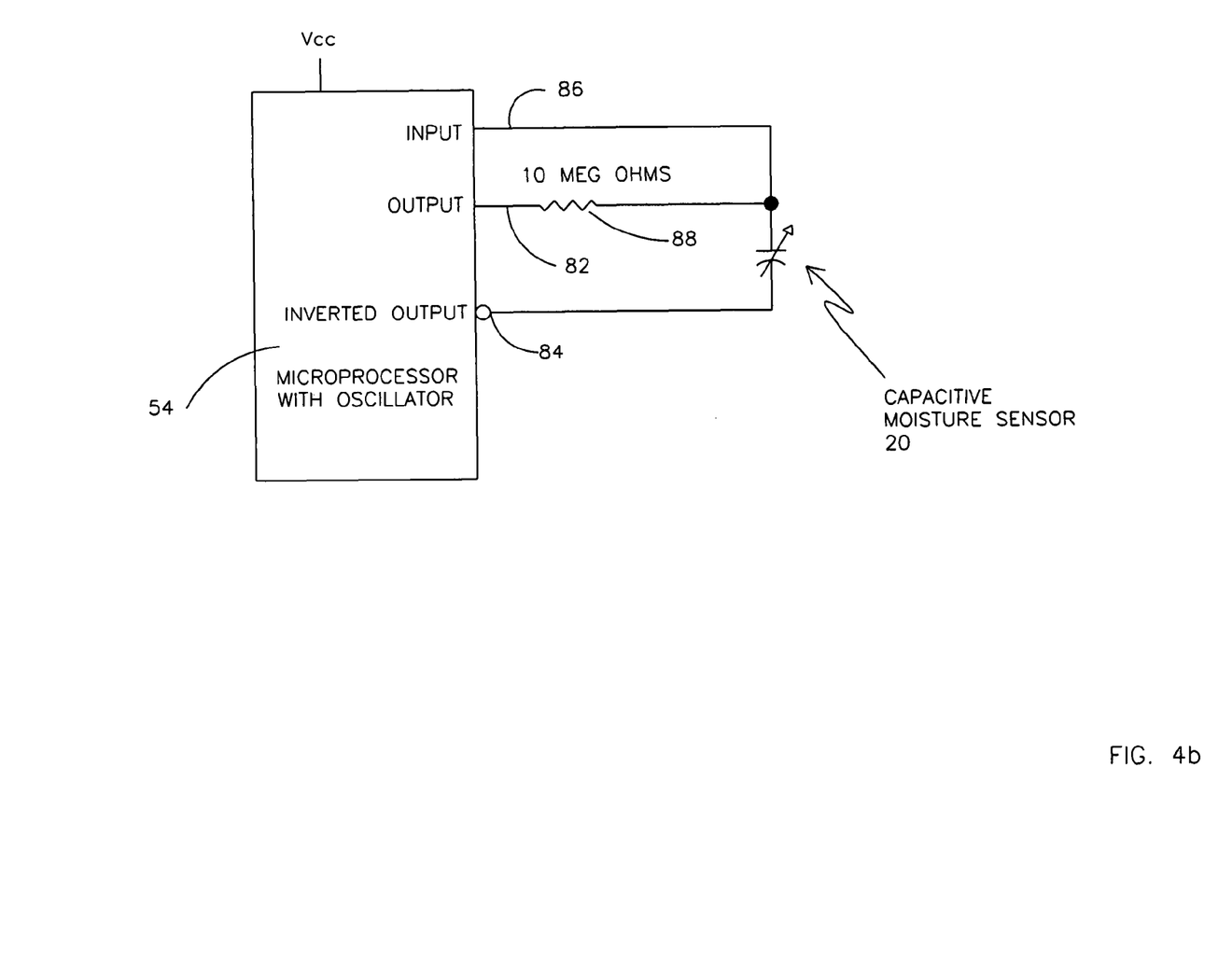
FIG. 4b is a schematic/block diagram of an embodiment including a capacitance moisture sensor and a microprocessor with an oscillator.

An alternative embodiment to determine change in capacitance of capacitance sensor 20 is shown in FIG. 4b. An AC signal generated by a program running on microprocessor 54 derived from the microprocessor clock is provided across outputs 82, 84 of microprocessor 54. Input 86 receives a signal resulting from RC delay across resistor 88 and capacitance sensor 20. This delay will change as moisture level increases between plates 20a, 20b of capacitance sensor 20. Microprocessor 54 detects the presence of moisture based on the delay between output signal 82 and input signal 86.

Uni-axial, bi-axial and triaxial strain gauges, such as those available from Vishay Micromeasurements, Raleigh, N.C. can be used, such as part numbers CEA-06-125UW-350, CEA-06-125UT-350, and CEA-06-125UA-350. Principal strain magnitudes and strain directions can be computed, as described in a textbook by James W. Dally & William F. Riley, "Experimental Stress Analysis", Third Edition, Chapter 9, Strain-Analysis Methods, pp 311-315 publisher: McGraw-Hill, Inc., NY, N.Y. (c) 1991, 1978, 1965 by Dally and Reilly.

These gauges include resistors, and the resistance changes both from changes in strain and from changes in moisture. The gauges do not include ability to detect moisture and do not include ability to distinguish a change in resistance due to a change in moisture from a change in resistance due to a change in strain. The deleterious effects of moisture and some ways to waterproof are described in the Dally & Riley book on pages 196-197. The present patent application provides a way to detect both strain and moisture and to protect against moisture.

Microprocessor 54 can receive data from capacitance sensor 20 related to any change in dielectric constant of its dielectric 36, 36', 36" and can report this change to base station 62, as shown in FIG. 4a. Information concerning a degraded capacitance sensor 20 that indicates the presence of moisture in dielectric 36, 36', 36" between plates 20a, 20b transmitted to base station 62, which will sound an alarm, store the data in memory, and mark that particular sensor assembly 32 for replacement. Sensor assemblies 32 that exhibit capacitance within a tolerance will remain in service transmitting data from surface 28 of structure 30 to which they are mounted. Thus, the present invention provides for self-testing and maintenance of sensors to ensure that they are reliably providing accurate data and that the bonding to structure surfaces has not degraded from moisture penetration.

FIG. 4a also shows an energy source, such as a battery or an energy harvesting device. These supply Vsupply to processor 54. Processor 54 can control power Vcc to capacitance signal conditioning 50 and A/D converter 52. Processor 54 can also control power Vcc' to strain gauge 22, strain gauge signal conditioning DC AMP, and the strain gauge A/D converter. Power Vtx can also be provided to transmitter 56 under control of processor 54. Also processor 54 can write data to non-volatile memory 57. A more detailed circuit diagram for a single strain gauge bridge is provided in FIG. 16 of the '505 patent. Multiple strain gauge bridges can be provided, as shown in FIG. 2 of the '108 patent, which includes a multiplexer.

Strain gauges have long been bonded to metal surfaces and the process for bonding a strain gauge to a metal surface is well known in the art. A combination of heat and pressure have been used to cure a thin glue line of two-part epoxy between the strain sensing element and the metallic substrate. Over 24 hours is needed at room temperature. About two hours is needed at an elevated temperature of about 150 C. Two-part epoxy with such extended cure time has been used for best results. However, this extended time process has not been easy to deploy in the field, especially if many strain sensor nodes need be attached to a structure. Compromises are typically made to facilitate quick curing, such as the use of cyanoacrylates (super-glues) or one-part epoxies. However, these room temperature, fast-curing adhesives do not provide as strong a bond as extended cure time two-part epoxy, greatly limiting the use of such glue-bonded strain gauges for long term structural health monitoring applications.

An improved system for in-field connection of a strain gauge to a metal or non-metal structural surface, using optimum epoxy formulations, and with subsequent waterproof encapsulation of the strain gauge and its signal conditioning, data logging, and wireless communication electronics, is needed. The finished package must be low profile, durable, low cost, and suitable for long term deployment. With the self-testing feature described herein above providing wirelessly transmission of information about the ingress of moisture, such a package has potential for much wider use individually or in a network of many such nodes than currently available packages. The application of wireless sensors with data logging elements, signal conditioning electronics and bidirectional electronics has been described in the '108 patent.

Figure 5:
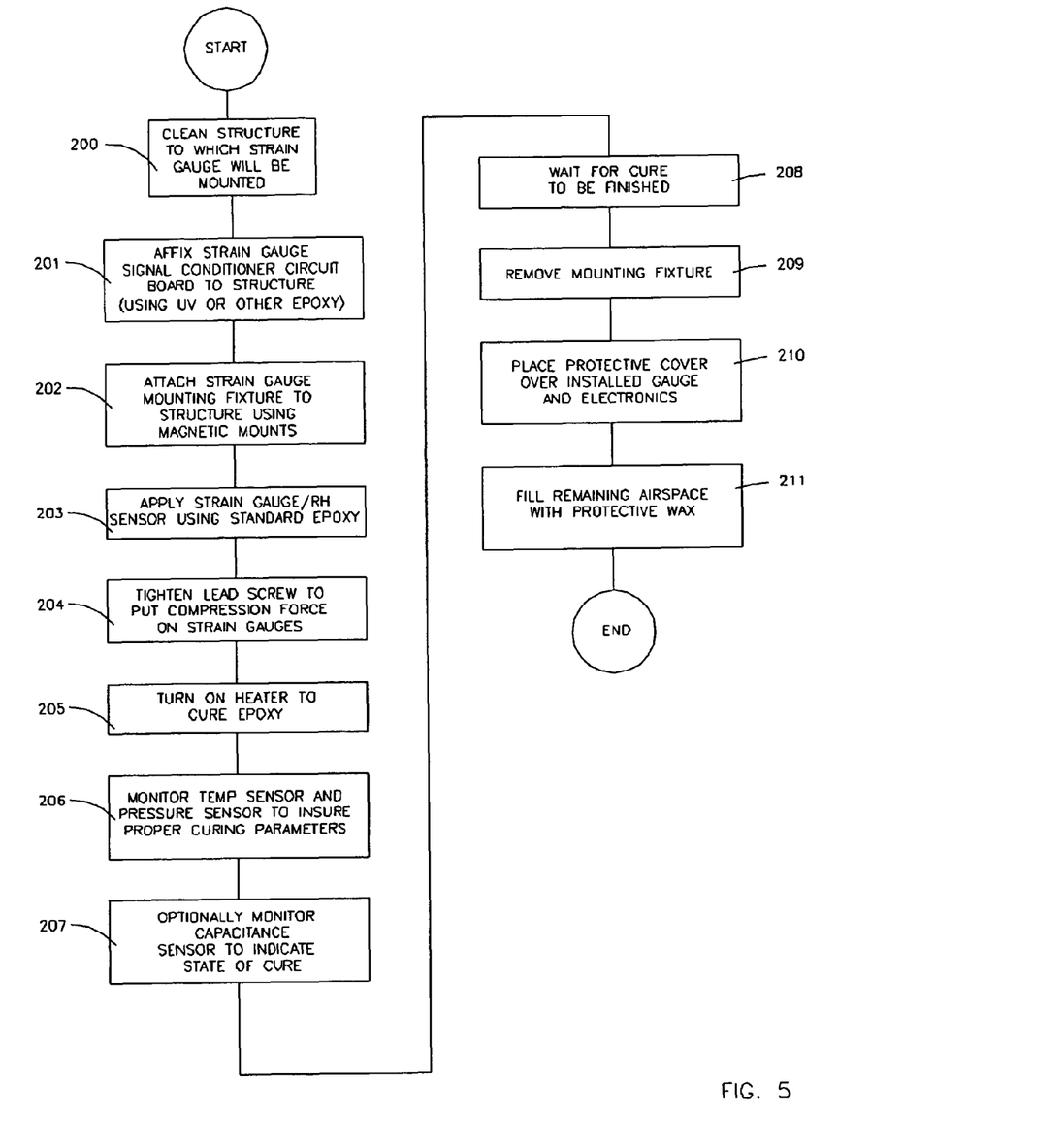
FIG. 5 is a flow chart showing an embodiment of a process to attach and protect a self-testing strain gauge node to a surface of a structure.

In addition to providing the self testing for moisture and the wireless transmission of this self-test data feature, the present inventors also provided an improved process to attach and protect their fully integrated, self-testing strain gauge sensor node to a surface of a structure, as shown in the flow chart in FIG. 5. In the first step, surface 28 of structure 30 to which sensor assembly 32 is to be mounted is properly cleaned, as shown in step 200. The surface can be a steel surface or it can be a plastic, composite or any other material.

In one embodiment strain gauge 22 and moisture sensing capacitance sensor 20 will have already been pre-wired to circuit board 59, or they can be integral with circuit board 59. Circuit board 59 contains supporting electronics and is fully tested for proper operation at the factory. Circuit board 59 can be fabricated of fiberglass materials, such as FR4 or of ceramic materials, such as low temperature co-fired ceramics. Circuit board 59 can also be fabricated of thin flexible insulative materials, such as polyimide. In this embodiment strain gauge 22, moisture sensing capacitance sensor 20, and circuit board 59 can be affixed to the structure using a UV-cured epoxy adhesive, as shown in step 201. UV light is provided to adhesive located under strain gauge 22, moisture sensing capacitance sensor 20, and edges of circuit board 59 accessible to UV light.

Figure 10A:
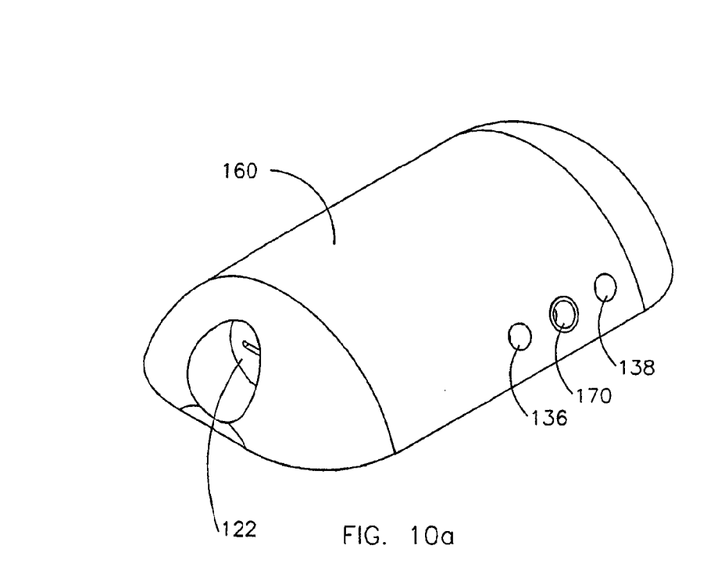
FIGS. 10a-10c are views of another embodiment of a tape-mounted protective cover for protecting a strain gauge and moisture sensor in which the printed circuit board is mounted to the protective cover, and the protective cover also includes an integrated replaceable sealed battery and openings for wax insertion.
Figure 10B:
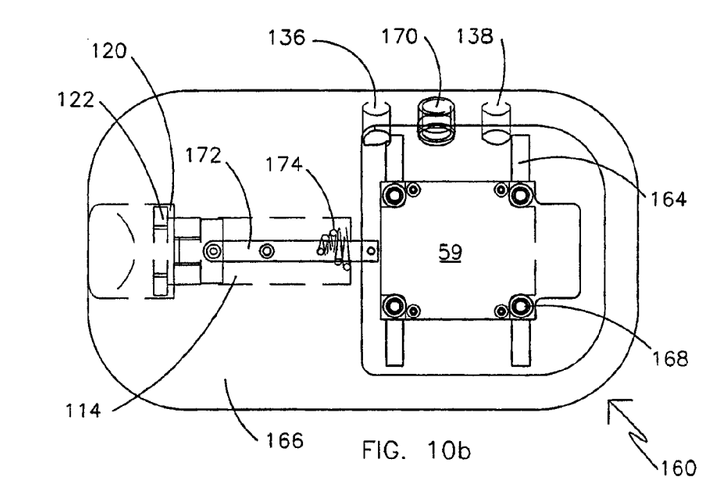

In another embodiment, circuit board 59 may be mounted to protective cover 89, as shown in FIGS. 10a-10b. In this embodiment lead wires from strain gauge 22 and moisture sensing capacitance sensor 20, affixed with a UV-cured epoxy adhesive, are plugged into a receptacle extending from circuit board 59. Circuit board 59 mounted in protective cover 89 can be protected with wax, silicone grease, or another protective material in the factory with only wires and/or a receptacle extending for mating with lead wires from strain gauge 22 and moisture sensing capacitance sensor 20. In this embodiment, protective cover 89 encloses strain gauge 22, moisture sensing capacitance sensor 20, circuit board 59, and lead wires there between.

The strain and moisture sensing elements are glued directly to the structure's steel substrate, as shown in steps 202 to, using a process more fully described herein below. For attachment to a steel portion of structure 32, magnetic mounts 90 are used to temporarily attach specially designed mounting fixture 92, as shown in step 202 and in FIG. 6. Fixture 92 includes frame 94 held in position by magnetic mounts 90.

Figure 6:
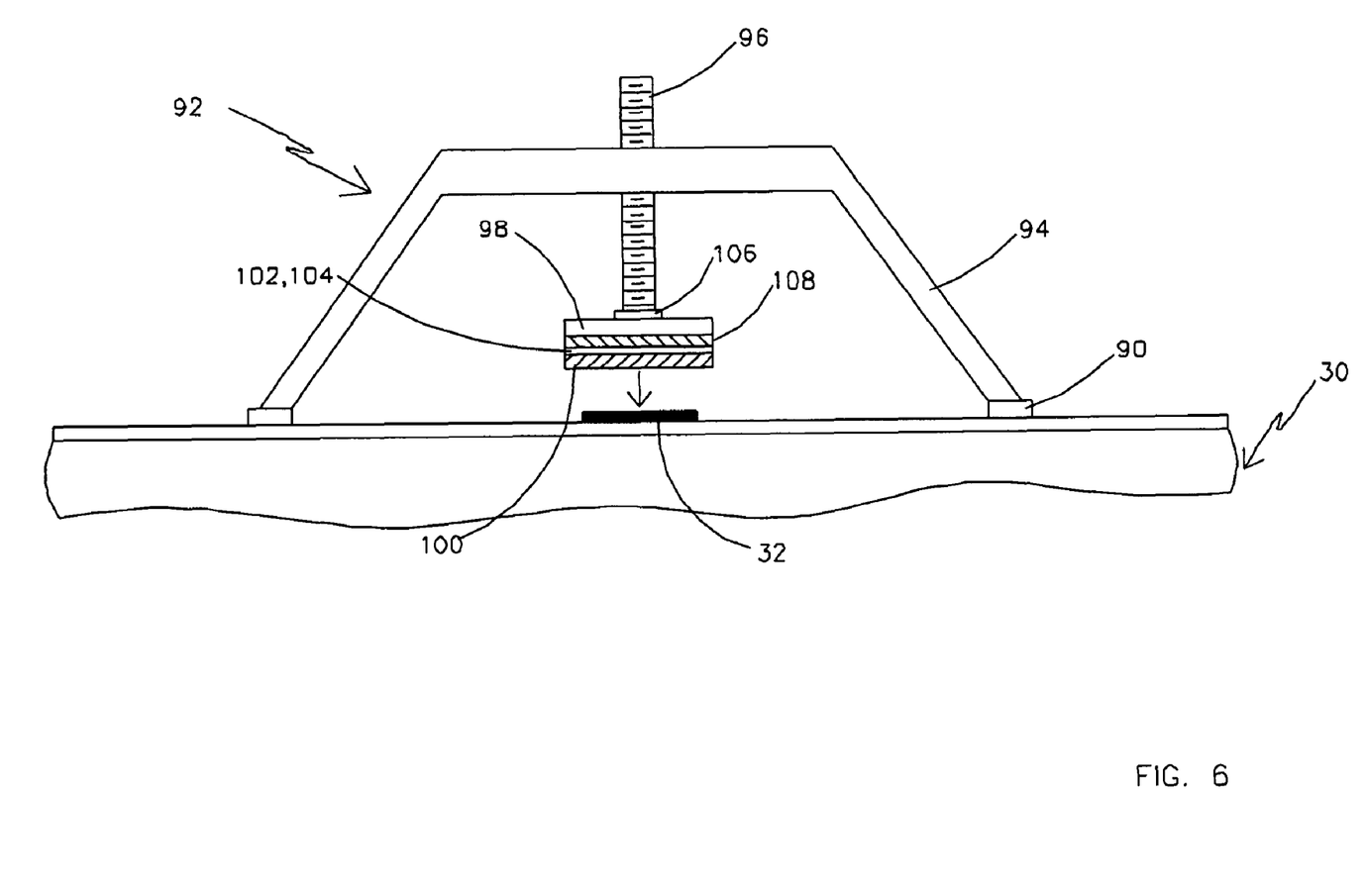
FIG. 6 is a cross sectional view of an embodiment of a temporary mounting fixture during use for attaching a strain gauge and moisture sensor to a steel structure.

Sensor assembly 32 is applied to surface 28 of structure 30 with epoxy as shown in step 203. Threaded plunger 96 provides compression on sensor assembly 32 including strain gauge 22 and capacitance moisture sensor 20. Threaded plunger 96 is tightened as shown in step 204, to provide compression force on sensor assembly 32.

Thermoelectric heating element 98 provides heat to more rapidly cure epoxy (not shown) beneath sensor assembly 32 while it is being compressed. Heating element 98 is turned on to cure epoxy as shown in step 205. Temperature and pressure are monitored with temperature sensor 104 and pressure sensor 102, as shown in step 206, and information may be fed back to heating element 98 and threaded plunger 96 or to the operator allowing control over the amount of pressure and heat applied to the assembly. Optionally, capacitance sensor 20 can be used to monitor the state of cure during this step, as shown in step 207 and waiting step 208, and to provide feedback about changes in the dielectric constant of the epoxy during the curing process, as described herein above for the embodiment of FIG. 3c. To accomplish this a temporary power source is provided to circuit board 59 during curing. Rubber pad 100 insures a stable pressure and an even pressure distribution during curing.

Swivel 106 allows aluminum plate 108 along with heating element 98 freedom of movement to accommodate a tilted surface. Aluminum plate 108 provides for uniform distribution of heat from heating element 98.

After curing is complete the mounting fixture is removed, as shown in step 209. Next protective cover 89 is installed on sensor assembly 32 and its supporting electronics on printed circuit board as shown in step 210. Finally remaining space in protective cover 89 is filled with wax, as shown in step 211.

An alternative method for quickly attaching a strain gauge to the substrate is to use an ultraviolet (UV) light curable epoxy. These epoxies are advantageous in that they are cured to provide a strong bond in a matter of seconds with exposure to UV light. They have advantage in that, before exposure to the UV light, the strain gauge can be re-positioned as needed, and then a few seconds exposure fixes the gauge in place. A potential problem is that UV light cannot penetrate the polyimide materials commonly used in strain gauge construction. However, the present inventors found that fiberglass resin backed strain gauges used for high performance transducers become clear when UV epoxy is placed on their backing, transmit UV, and allow UV curable epoxy to be used.

In preliminary experiments the present inventors bonded several fiberglass resin backed strain gauges from Micro-Measurements, Inc., Atlanta, Ga., with a UV curable epoxy from Epoxy Technology, Inc. Destructive testing of the glue line indicated that a strong bond had been achieved beneath the strain sensing elements. However, testing showed delamination and that the epoxy had not been cured beneath the large copper bonding tab areas. Clearly the UV light did not reach these areas. The present inventors designed a custom strain gauge with windows or stripes of metal in the copper bonding pad area to let sufficient UV light through to cure the epoxy in these areas, as shown in FIG. 2b. In addition to soldering, attachment of lead wires to these pads can be accomplished with electrically conductive UV curable epoxy, available from Allied Chemical Co., division of Honeywell, Plymouth, Minn.

Figure 7:
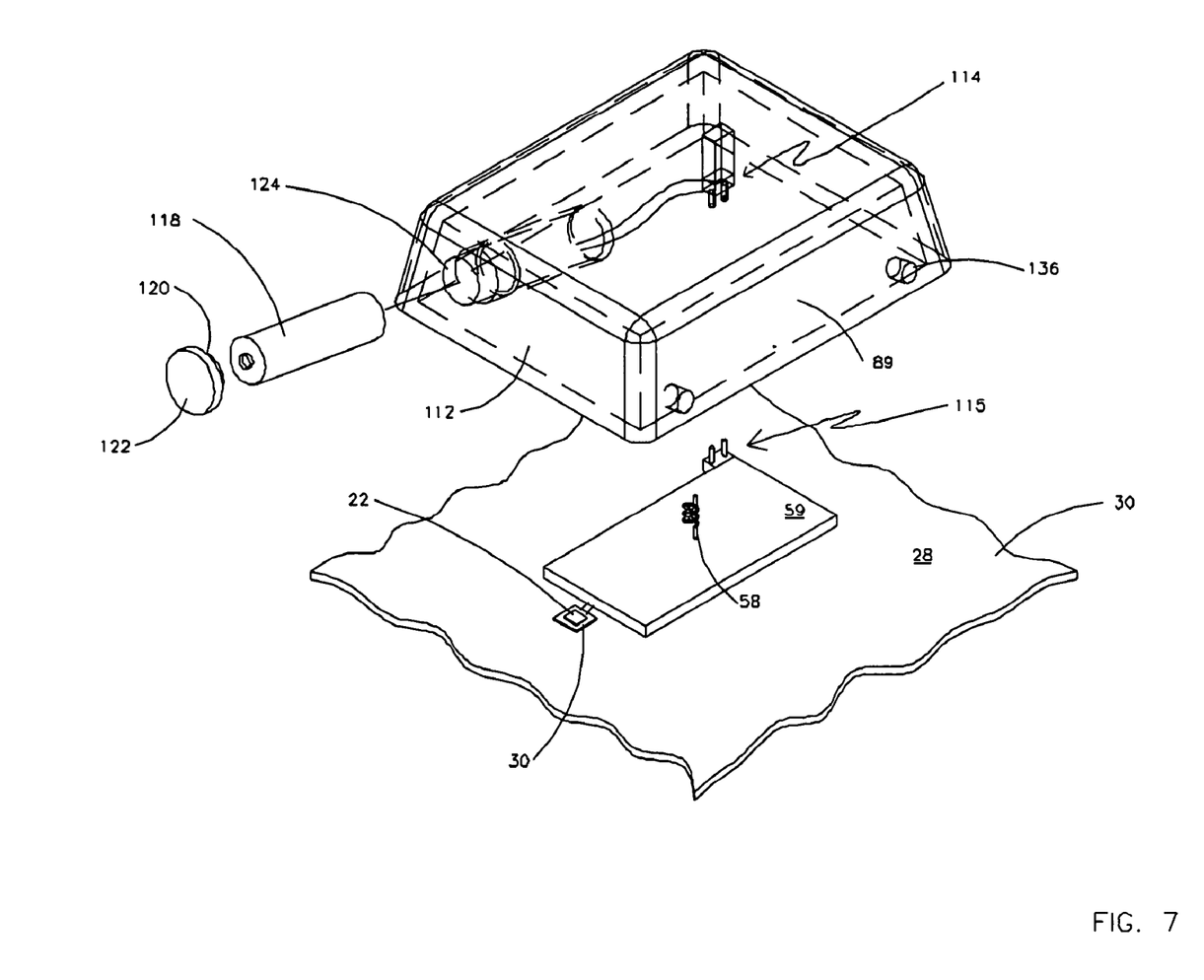
FIG. 7 is a three dimensional view of an embodiment of a tape mounted protective cover for protecting a strain gauge and moisture sensor in which the protective cover includes an integrated replaceable sealed battery and openings for wax insertion.

In the next step in the packaging process protective cover 89 is provided and mounted on surface 28 of structure 30 to enclose sensor assembly 32 and circuit board 59 with its antenna 58, as shown in step 204 and in FIG. 7. Preferably, cover 89 is fabricated of a clear polycarbonate material. Protective cover 89 can include high strength aggressive contact adhesive tape 112, available from 3M Corp., Minneapolis, Minn., on its bottom edges for securing to surface 28 of structure 30. The technician doing the mounting will remove the protective polyethylene film (not shown) covering adhesive tape 112 and visually align battery compartment plug 114 with its mate battery connection header 115 on circuit board 59. Battery compartment plug 114 is wired to battery compartment 116 into which battery 118 can be inserted and sealed with O-ring seal 120 on threaded battery cover 122 that encloses battery 118 in threaded hole 124. Cover 89 will then be pressed onto surface 28 of structure 30 to provide a high strength bond there between.

To maintain a long life for battery 118, the power management paper describes techniques to reduce power consumption, extending the life of battery 118. These energy saving strategies are also useful when energy harvesting systems are deployed, such as those describes in the '693 patent to Hamel and the '505 patent to Arms. The energy harvesting methods could be used to eliminate battery 118 and energy can be stored on a capacitor, as described in these patent applications. The present inventors found that low leakage electrochemical batteries exhibited characteristics that were favorable for use with energy harvesting. Battery 118 can be a rechargeable battery and energy harvesting can be used to recharge battery. Alternatively, electromagnetic energy can be provided to recharge battery 118 as described in the '730 application. Alternatively, a charger can be plugged into the sensor node to charge battery 118.

The '505 patent also provides a scheme for performing automatic and wireless shunt calibration and for adjusting offsets and gains wirelessly.

Figure 8:
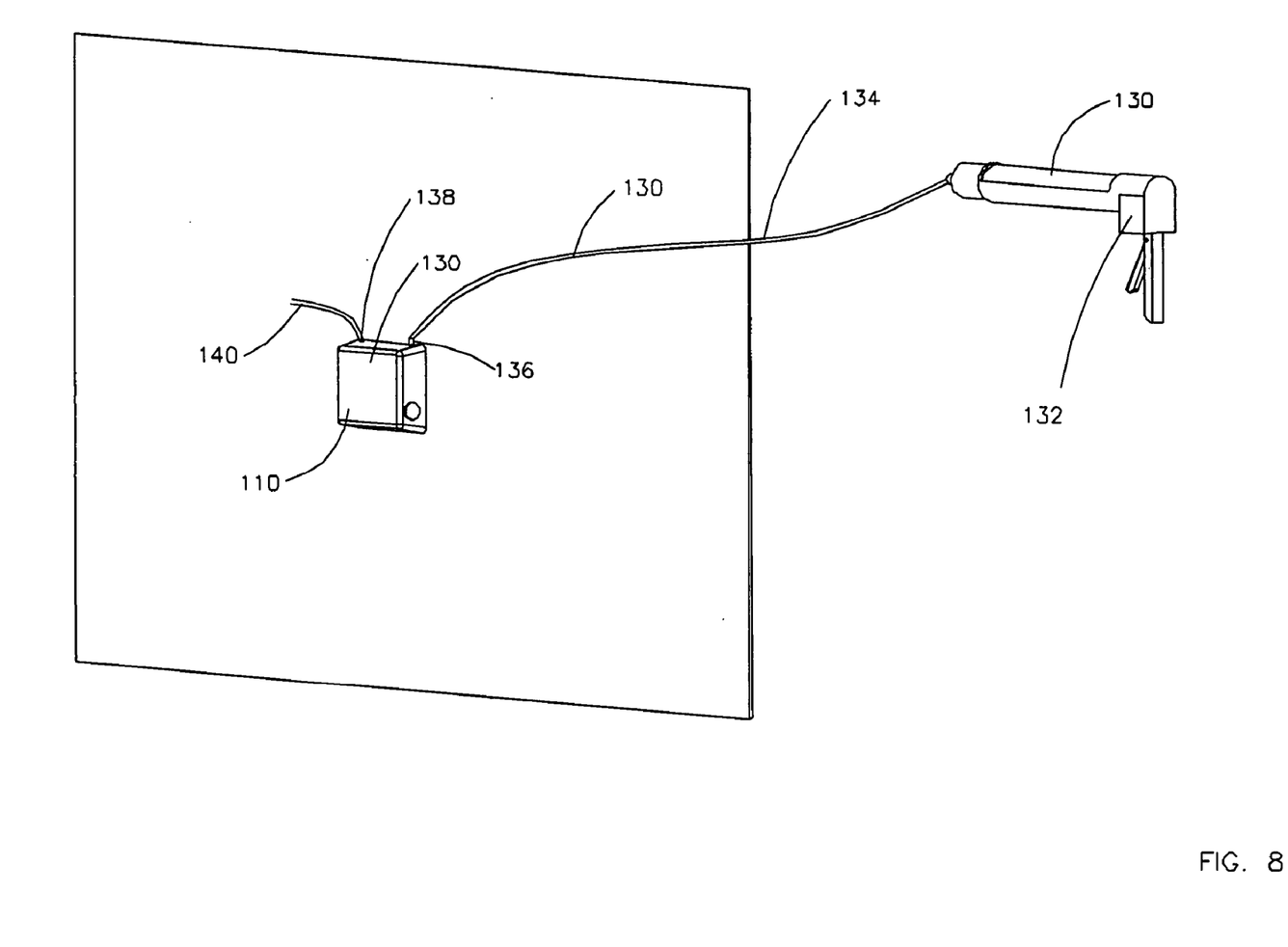
FIG. 8 is a three dimensional view of an embodiment of a process for filling a protective cover with molten wax.

Next, wax moisture barrier 130 is provided to protect components on circuit board 59 and sensor assembly 32 including strain sensor 22 and capacitance sensor 20 as shown in FIGS. 7, 8. It is well known that microcrystalline wax is the most effective organic barrier material currently available for protecting strain gauge circuits from moisture. Wax is reported to be superior to butyl rubber and silicone rubber because both of these materials absorb moisture from the environment while wax rejects moisture. But there are several disadvantages of using wax barriers, including weak mechanical properties, a tendency to become brittle at extremely low temperatures, and a low melting point of 170 deg F. or 80 degrees C.

The present inventors found that problems associated with the weak mechanical strength of wax 130 could be avoided by providing wax 130 inside polycarbonate protective cover 89, 110 to control and protect wax 130 from mechanical damage as shown in FIG. 8. They provided injection gun 132 filled with liquid polycrystalline wax 130 to fill protective cover 89, 110 and encapsulate sensor assembly 32 and electronics on circuit board 59 inside cover 89, 110 after cover 89, 110 has been mounted to surface 28 of structure 30. Inlet filling tube 134 is connected to threaded wax inlet hole 136 of protective cover 89, 110 using polytetraflourethylene (Teflon) tubing. Molten wax 130 is injected into cover 89, 110 through inlet hole 136 until cover 89, 110 is visually full of wax 130 and wax 130 begins to be extruded out of outlet hole 138 and into outlet tube 140 in cover 89, 110, as shown in FIG. 8.

Figure 9A:
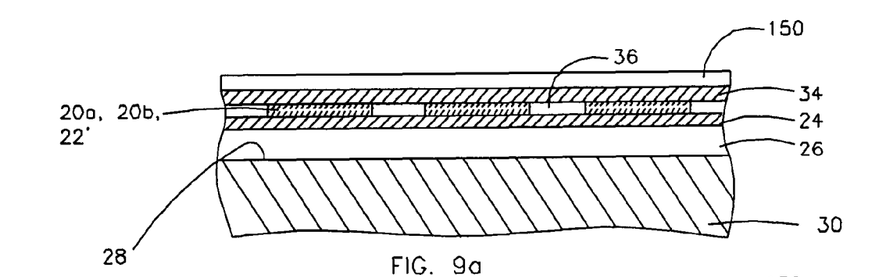
FIGS. 9a-9c are cross sectional views similar to those of FIGS. 3a-3c with an additional thin film of wax, grease, Waxoyl or anticorrosion formula.
Figure 9B:
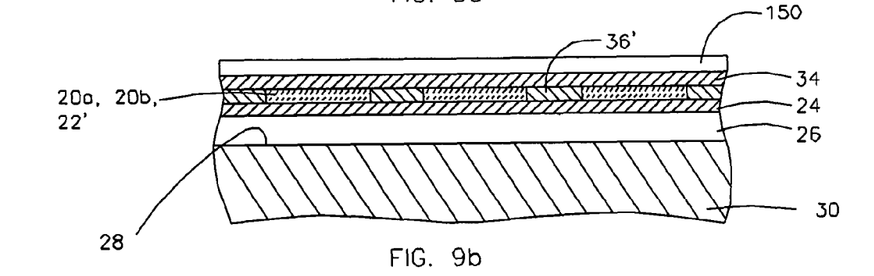
Figure 9C:
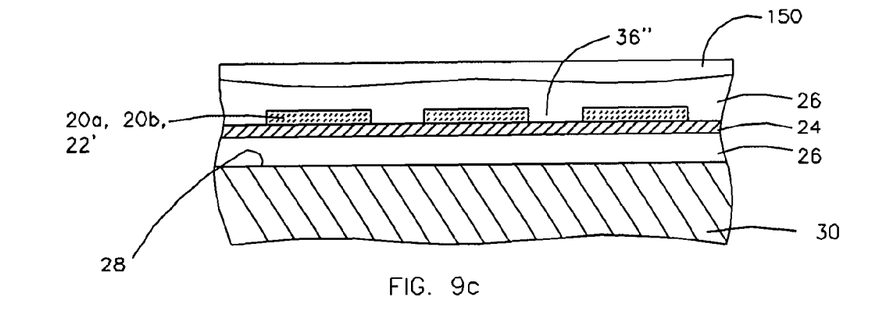

The present inventors found that a variety of protective materials can be used, including wax, grease, a foam protective agent, and anticorrosion formulas, such as ACF-50. Thin film 150 of wax, grease, Waxoyl or anticorrosion formula is shown in FIGS. 9a-9c. Waxoyl is available from Waxoyl AG, Basel, Switzerland. ACF-50 is available from Lear Chemical Research Corp, Mississauga, Ontario, Canada.

The foam protective agent can be a urethane expanding foam, which can be obtained from a manufacturer, such as Fomo Products, Inc., Norton, Ohio. This urethane foam is available in many forms although a 2 component aerosol would be easiest to use in this application due to the 2 minute cure time and its ability to be sprayed through a long tube into the enclosure opening. This material is water proof, expanding, bonds to many surfaces, and is slightly flexible. The expansion will ensure that all of the components including the strain gauge and electronics are thoroughly coated.

In addition, vent 170, such as a vent provided by W. L. Gore and Associates, Inc., Newark, Del., may be provided to provide pressure equalization without allowing moisture to pass, as shown in FIGS. 10a, 10b, 10c.

Protective cover 160 has a rounded convex outer surface with curvature extending from the structure surface to which it is attached, as shown in FIG. 10a. This shape facilitates transfer of many impact loads that might shear adhesive bond 162 into compression loads. Thus a falling object is less likely to cause breakage of adhesive tape 112 holding protective cover 160 to the structure surface. Protective cover 160 includes printed circuit board 59 mounted to mounting bosses 164 on bottom surface 166 with screws 168, as shown in FIG. 10*b*.

Figure 10C:
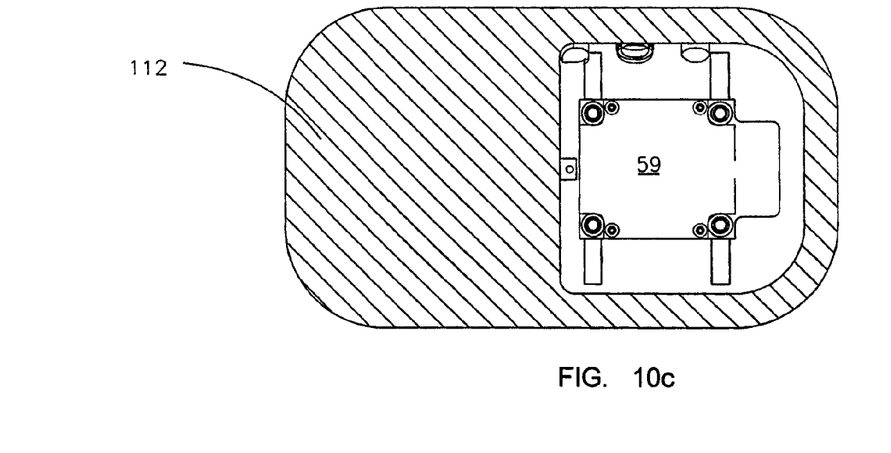

Protective cover 160 also includes adhesive tape 112 for adhesively attaching protective cover 160 to a structure surface, as shown in FIG. 10*c*. Inlet hole 136 and outlet hole 138 are provided as described herein above, as shown in FIG. 10*a*. Inlet hole 136 and outlet hole 138 may be threaded to accommodate a plug and o-ring for sealing purposes after filling is complete. Vent 170, such as a vent provided by W.L Gore and Associates, Inc. Newark, Del., can be provided as well.

Battery compartment 114 is also provided with its cover 122 and o-ring seal 120. Positive return 172 extends from the positive terminal of battery 118 to printed circuit board 59. Spring 174 for the negative terminal of battery 118 is also provided.

While the disclosed methods and systems have been shown and described in connection with illustrated embodiments, various changes may be made therein without departing from the spirit and scope of the invention as defined in the appended claims. The examples given are intended only to be illustrative rather than exclusive.

What is claimed is:

1. A device comprising a structure, a strain sensor, a light curable adhesive, a moisture barrier, and a protective cover, wherein said structure has a structure surface, wherein said light curable adhesive bonds said strain sensor to said structure surface, wherein said moisture barrier is located to protect said light curable adhesive, wherein said protective cover is bonded to said structure surface, wherein said protective cover extends over said strain sensor and over said moisture barrier, wherein said moisture barrier substantially fills said protective cover, wherein said protective cover includes a first port and a second port, wherein said first port is for filling said protective cover with said moisture barrier and wherein said second port is for providing an exhaust while filling.

2. A device as recited in claim 1, wherein said light curable adhesive includes UV light curable adhesive.

3. A device as recited in claim 2, wherein said strain sensor has a backing, wherein said backing transmits UV light.

4. A device as recited in claim 3, wherein said backing includes fiberglass.

5. A device as recited in claim 3, further comprising a bonding pad on said backing for providing electrical contact to said strain gauge, wherein said bonding pad includes at least one from the group consisting of a window and a stripe for facilitating UV light transmission to said UV light curable adhesive.

6. A device as recited in claim 1, wherein said moisture barrier comprises a wax material.

7. A device, as recited in claim 1, wherein said moisture barrier includes at least one from the group consisting of wax, grease, a foam, and waxoyl.

8. A device, as recited in claim 1, wherein said protective cover is a preformed protective cover.

9. A device, as recited in claim 8, wherein said preformed protective cover includes a vent to provide pressure equalization without allowing moisture to pass.

10. A device, as recited in claim 8, wherein said preformed protective cover is fabricated of polycarbonate.

11. A device, as recited in claim 8, wherein no wires exit said preformed protective cover.

12. A device, as recited in claim 8, wherein said preformed protective cover has a convex outer surface with said convex curvature extending from said structure surface.

13. A device as recited in claim 8, wherein said preformed protective cover has a shape wherein all of said preformed protective cover facing a shear-oriented impact load transfers said shear-oriented impact load into a compression load.

14. A device as recited in claim 1, wherein said moisture barrier comprises a thin layer on said component.

15. A device as recited in claim 1, further comprising a moisture detector located to detect moisture in a vicinity of said light curable adhesive.

16. A device as recited in claim 1, further comprising an electronic circuit connected to receive data from said strain sensor wherein said moisture barrier is located to protect said electronic circuit.

17. A device as recited in claim 16, wherein said electronic circuit includes a microprocessor and signal conditioning.

18. A device as recited in claim 17, wherein said electronic circuit includes a transmitter.

19. A device, as recited in claim 1, wherein said structure includes a civil structure.

20. A device, as recited in claim 1, wherein said structure includes a machine.

21. A device, as recited in claim 1, wherein said structure includes at least one from the group consisting of a building, a bridge, a vehicle, construction equipment, and excavation machinery.

22. A device, as recited in claim 21, wherein said vehicle includes a car, a truck, and a ship.

23. A device, as recited in claim 1, wherein said structure includes a spinning shaft.

24. A device, as recited in claim 23, wherein said spinning shaft is part of at least one from the group consisting of a motor, a pump, and a generator.

25. A device comprising a structure, a strain sensor and a light curable adhesive, wherein said structure has a structure surface, wherein said light curable adhesive bonds said strain sensor to said structure surface, wherein said light curable adhesive includes UV light curable adhesive, wherein said strain sensor has a backing, wherein said backing transmits UV light.

26. A device as recited in claim 25, wherein said backing includes fiberglass.

27. A device as recited in claim 25, further comprising a bonding pad on said backing for providing electrical contact to said strain gauge, wherein said bonding pad includes at least one from the group consisting of a window and a stripe for facilitating UV light transmission to said UV light curable adhesive.

28. A device comprising a structure, a strain sensor, a light curable adhesive, a moisture barrier, and a protective cover, wherein said structure has a structure surface, wherein said light curable adhesive bonds said strain sensor to said structure surface, wherein said moisture barrier is located to protect said light curable adhesive, wherein said protective cover is bonded to said structure surface, wherein said protective cover extends over said strain sensor and over said moisture barrier, wherein said protective cover is a preformed protective cover, and wherein said preformed protective cover includes a vent to provide pressure equalization without allowing moisture to pass.

29. A device comprising a structure, a strain sensor, a light curable adhesive, a moisture barrier, and a moisture detector, wherein said structure has a structure surface, wherein said light curable adhesive bonds said strain sensor to said structure surface, wherein said moisture barrier is located to protect said light curable adhesive, wherein said moisture detector is located to detect moisture in a vicinity of said light curable adhesive.

* * * * *